US006969592B2

(12) United States Patent
Fowst et al.

(10) Patent No.: US 6,969,592 B2
(45) Date of Patent: Nov. 29, 2005

(54) METHOD FOR PREDICTING THE SENSITIVITY TO CHEMOTHERAPY

(75) Inventors: Camilla Fowst, Milan (IT); Maria Christina Rosa Geroni, Milan (IT); Jennifer Margaret Tursi, Milan (IT); Franzanne Vreeland, Martinsville, NJ (US)

(73) Assignees: Pharmacia Italia S.p.A., Milan (IT); Pharmacia & Upjohn Company LLC, Kalamazoo, MI (US)

( * ) Notice: Subject to any disclaimer, the term of this patent is extended or adjusted under 35 U.S.C. 154(b) by 439 days.

(21) Appl. No.: 09/962,611

(22) Filed: Sep. 26, 2001

(65) Prior Publication Data

US 2003/0096325 A1 May 22, 2003

(51) Int. Cl.⁷ .................................................. C12Q 1/48
(52) U.S. Cl. ........................................ 435/15; 435/193
(58) Field of Search ............................. 435/15, 6, 193

(56) References Cited

U.S. PATENT DOCUMENTS

| 5,646,177 | A |   | 7/1997 | Koch et al. |
| 5,880,097 | A |   | 3/1999 | Kauvar et al. |
| 6,013,462 | A | * | 1/2000 | Kauvar et al. ................ 435/7.4 |
| 6,576,612 | B1 | * | 6/2003 | Fowst et al. ................... 514/18 |
| 6,756,063 | B2 | * | 6/2004 | Kiss ........................... 424/630 |

FOREIGN PATENT DOCUMENTS

| EP | 0 246 868 | 11/1987 |
| EP | 0 265 719 | 5/1988 |
| EP | 0 420 121 | 4/1991 |
| GB | 2 178 036 | 2/1987 |
| WO | 0 388 948 | 9/1990 |
| WO | WO 90 11277 A | 10/1990 |
| WO | WO 96 05196 A | 2/1996 |
| WO | WO 97 28123 | 8/1997 |
| WO | WO 97 43258 | 11/1997 |
| WO | WO 98 04524 A | 2/1998 |
| WO | WO 98 21202 A | 5/1998 |
| WO | WO 99/34796 A | 7/1999 |
| WO | WO 99 50265 A | 10/1999 |
| WO | WO 99 50266 | 10/1999 |
| WO | WO 00 06541 | 2/2000 |
| WO | WO 00 6542 | 2/2000 |
| WO | WO 01 40181 A | 6/2001 |
| WO | WO 01 85144 | 11/2001 |

OTHER PUBLICATIONS

Stewart D. Non–Chemotherapeutic Agents That Potentiate Chemotherapy Efficacy. Cancer Treatment Reviews 1989, vol. 16, 1–40.*

Tsuchida S. Elevation of the Placental GST in Tumor Tussies and the Levels in Sera of Patients with Cancer. Cancer Research, 49, 5225–9, 1989.*

Geroni C. PNU–166196 A Novel DNA Minor Groove Binder With Enhanced Activity in Tumors Expressing High GST levels. Int J of Molecular Medicine 2001 8(Suppl 1) S10, Abstract 121.*

Geroni C. PNU–166196: A Novel Antitumor Agent Whose Cytotoxicity is Enhanced in Tumor Cells with High Levels of Glutathione. Tumori Jul.–Aug., 2000. 86(4)Suppl 1, 41–42.*

Gorozhanskaia E. TheRole of Glutathione and Glutathione S Transferase in Cancer Drug Resistance. Bulletin of Experimental Biology and Medicine. May 1998 125(5)562–5.*

Sola F et al: "The antitumor efficacy of cytotoxic drugs is potentiated by growth–factor–complexing molecule" Cancer Chemotherapy and Pharmacology, vol. 43, No. 3, 1999, pp. 241–246, XP002104215. ISSN: 0344–5704.

Zou J P et al: "Distamycin A derivatives potentiate tumor–necrosis factor activity via the modulation of tyrosine phosphorylation" International Journal fo cance, New York, NY, US, vol. 72, No. 5, 1997, pp. 810–814, XP002104217 ISSN: 0020–7136.

Tagliabue G et al: "Combination of the New Minor Groove Alkylator Tallimustine and Melphalan" European Journal of Cancer, Pergamon Press, Oxford, GB, vol. 33, No. 2, (Feb. 1997), pp. 284–287, XP004282511 ISSN: 0959–8049.

Geroni Cristina et al: "Antitumor activity of PNU–166196, a novel DNA minor groove binder selected for clinical development." Proceedings of the American Association for Cancer Research Annual, No. 41, (Mar. 2000), pp. 425–426, XP001039861 91 st Annual Meeting of the American Association for Cancer Research.; San 2000, Mar. 2000 ISSN: 0197–016X, abstract only.

Baradi, Pier Giovanni et al: "Synthesis and antitumor activity of novel distamycin derivatives"Bioorg. Med. Chem. Lett. (1996), 6(11), 1241–1246 XP004134862 p. 1241, paragraph 2 example SCHEME1 p. 1244, paragraph 1 table 1 page 1244, paragraph 4 –p. 1245, paragraph 1.

Cozzi P et al: XP004200573 "Cytotoxic alpha–Bromoacrylic Derivatives of Distamycin Analogues Modified at the Amidino Moiety" Bioorganic & Medicinal Chemistry Letters, Oxford, GB, vol. 10, No. 11, (Jun. 2000), pp. 1273–1276, ISSN: 0960–894X.

Cozzi P et al: XP004200572 "Cytotoxic Halogenoacrylic Derivatives of Distamycin A" Bioorganic & Medicinal Chemistry Letters, Oxford, GB, vol. 10, No. 11, (Jun. 2000), pp. 1269–1272, ISSN: 0960–894 X.

(Continued)

*Primary Examiner*—Ralph Gitomer
(74) *Attorney, Agent, or Firm*—Scully, Scott, Murphy & Presser

(57) ABSTRACT

The present invention relates to the field of cancer treatment and, more particularly, it relates to a method for predicting the sensitivity towards chemotherapy of a patient, by measuring glutathione (GSH) blood levels of the said patient undergoing chemotherapeutic treatment.

12 Claims, 2 Drawing Sheets

OTHER PUBLICATIONS

Figure 1:
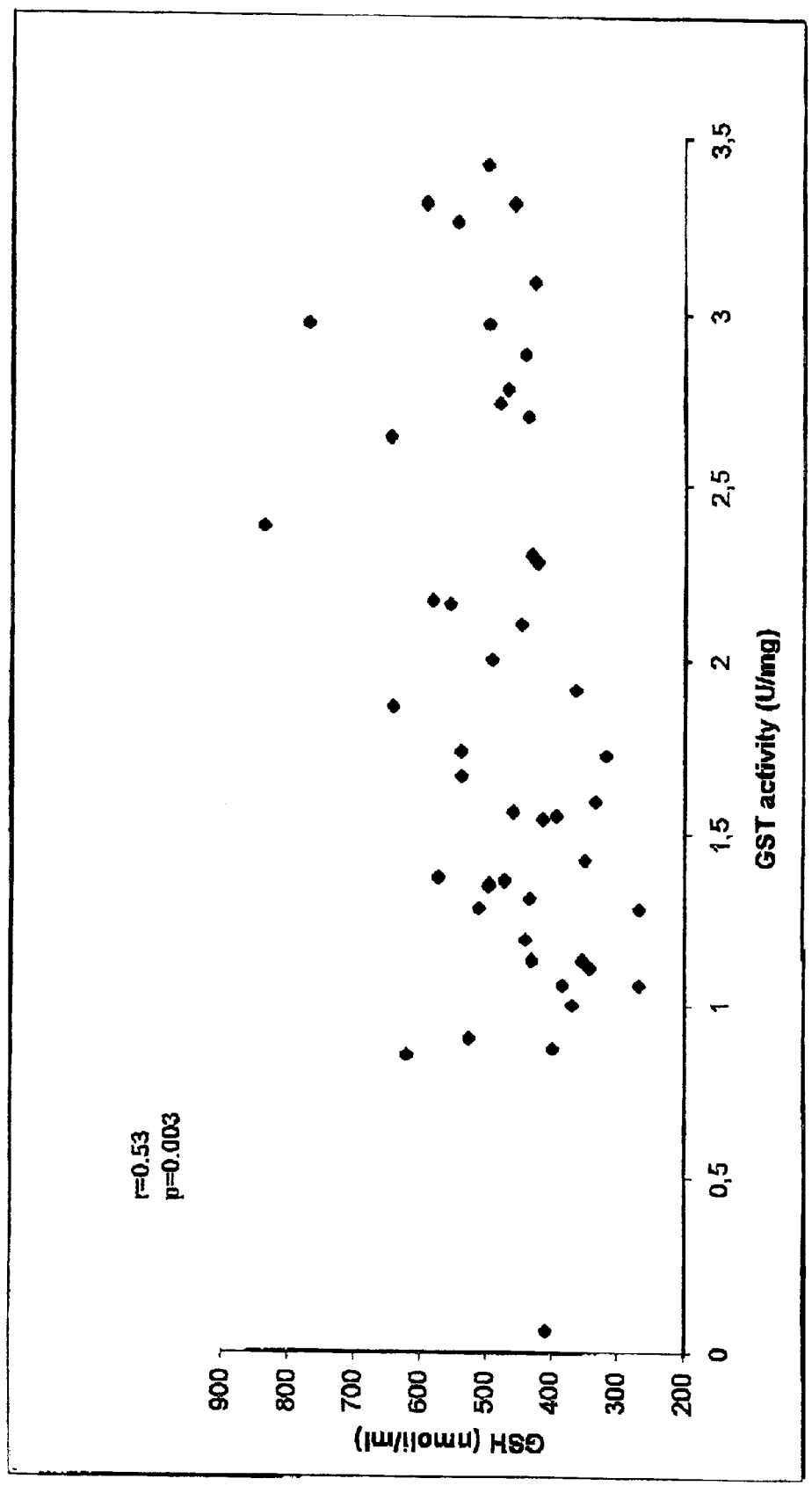

Catharina J A Van Moorsel et al: XP002110339 "Gemcitabine: Futrue Prospects of Single–Agent and Combination Studies" Oncologist, Alphamed Press, US, vol. 2, No. 3, 1997, pp. 127–124, ISSN: 1083–7159.

Budavari S (ED): XP002191966 "The Merck Index (12th Edition)" Merck Index, Encyclopedia of Chemicals, Drugs, and Biologicals, 13th. Edition 1996, Whitehouse Station, Merck & Co, US, vol. ED. 13, 2001, p. 4206 ISBN: 0–911910–12–3.

Mosconi A M et al: XP004282426 "Combination Therapy with Gemcitabine in Non–small Cell Lung Cancer" European Journal of Cancer, Pergamon Press, Oxford, GB, vol. 33, (Jan. 1997), pp. S14–S17, ISSN: 0959–8049.

D'Alessio, Roberto et al: "Structure–activity relationship of novel distamycin A derivatives: Synthesis and antitumor activity" Bioorg. Med. Chem. Lett. (1994), 4(12), 1467–72, XP000671766.

Stewart D J et al: "Non–Chemotherapeutic Agents that Potentiate Chemotherapy Efficacy" Cancer Treatment Reviews, vol. 16, No. 1, 1989, pp. 1–40, XP001039737 ISSN: 0305–7372 p. 18, paragraph 3 –p. 19, paragraph 1.

Colella, G. et al: "Mismatch repair deficiency is associated with resistance to DNA minor groove alkylating agents" BR. J. Cancer (1999), 80(3/4), 338–343, XP001039733.

Giustianna Maria et al: "In vivo induction of apoptosis with PNU–166196 in human ovarian carcinoma xenografts." Proceedings of the American Association for Cancer Research Annual, No. 41, (Mar. 2000), p. 825 XP001039865 91st Annual Meeting of the American Association for Cancer Research.: San Francisco, California, USA; Apr. 1–5, 2000, Mar., 2000 ISSN: 0197–016x, abstract.

Tsuchida S et al: "Elevation of the Placental Glutathione–S–Transferase Form GST–Pl in Tumor Tissues and the Levels in Sera of Patients with Cancer" Cancer Research, vol. 49, No. 18, 1989, pp. 5225–5229, XP001039783 ISSN: 0008–5472 abstract p. 5225, column 1, paragraph 1 p. 5228, column 1, paragraph 1 p. 5228, column 2, paragraph 2.

Cozzi P: "A new class of cytotoxic DNA minor groove binders: alpha–halogenoacrylic derivatives of pyrrolecarbamoyl oligomers." FARMACO, (Jan.–Feb. 2001) 56 (1–2) 57–65., XP001039805 abstract p. 58, column 2, paragraph 4 p. 59, column 1, paragraph 1 figure 5 p. 60, column 1, paragraph 2 –p. 61, column 1, paragraph 4 tables 2,3 p. 62, column 2, paragraph 3 figures 9, 10 table 5 p. 63, column 1, paragraph 1 –column 2, paragraph 2.

Baraldi, Pier Giovanni et al: "Synthesis and Antitumor Activity of New Benzoheterocyclic Derivatives of Distamycin A" J. Med. Chem. (2000), 43(14), 2675–2684 , (Jul. 13, 2000), XP001039581 abstract p. 2676, column 1; tables p. 2676, column 1, paragraph 1 tables 1,2 p. 2678, column 2, paragraph 5 –p. 2679, column 1, paragraph 1 p. 2680, column 2, paragraph 3.

Boger et al., "Total Synthesis of Distamycin A and 2640 Analogues: A Solution–Phase Combinatorial Approach to the Discovery of New Bioactive DNA Binding Agents and Development of a Rapid, High–Trroughput Screen for Determining Realtive DNA Binding Affinity or DNA Binding Sequence Selectivity", J. Am. Chem. Soc. 2000, 122, 6382–6394.

* cited by examiner

METHOD FOR PREDICTING THE SENSITIVITY TO CHEMOTHERAPY

The present invention relates to the field of cancer treatment and, more particularly, it relates to a method for predicting the sensitivity towards chemotherapy of a patient, by measuring glutathione (GSH) blood levels of the said patient undergoing chemotherapeutic treatment.

The levels of glutathione (GSH) or GSH-related enzyme glutathione-S-transferase (GST) are known in the art to be correlated with the response to cytotoxic antitumor treatments since high levels of GSH or GST confer resistance to several antitumor drugs such as, for instance, alkylating agents (e.g. melphalan, chlorambucil, cyclophosphamide, ifosfamide mustards, BCNU), platinum complexes (e.g. cisplatin, carboplatin and oxaliplatin) and anthracyclines (e.g. doxorubicin, epirubicin, idarubicin and daunorubicin) [*Biochem. Pharmacol* 35: 3405–3409 (1986)].

Both GSH and GST are ubiquitously present in several human tissues such as, for instance, blood cells, plasma, serum, circulating blasts and pathologic (tumor) tissues.

See, for general references to GSH and GST, *Cancer Res.* 54: 4313–4320 (1994); *Brit. J. Cancer* 72(2): 324–326 (1995); *Drug Discovery Today* 3:113–121 (1998).

GST, and most prominently GST-π, are present at high levels in a preponderance of tumor types. Increased levels of GSH and activity of GST in comparison to normal tissues has been found in several tumor types comprising, for instance, gastrointestinal tumors, uterine and ovarian cancers, head and neck cancer, lung carcinomas, sarcomas and liver tumors [*Cancer Res.* 49:5225–5229 (1989); *Clinical Reviews in Biochemistry and Molecular Biology* 27(4.5): 337–386 (1992)].

GSH plays a crucial protective role against cellular injury produced by a number of toxic insults. Preclinical and clinical studies have established a correlation between GSH/GST over expression and cancer or cancer response to chemotherapy.

Alterations of the GSH-based detoxification system (consisting of GSH and GSH related enzymes, GSTs) have been also associated with varying responsiveness to several antineoplastic agents.

So far, because of the low rate of responsiveness to conventional chemotherapy in those tumors over expressing GSH/GST, the identification of new markers predicting sensitivity to therapy is of utmost importance.

Of additional importance was the requirement to identify these new predictive markers from a relatively non-invasive source, for instance blood or blood component, to allow these predictive markers to be readily analyzed for the evaluation of chemotherapy sensitivity.

We have now found that GST activity in tumor tissues is strongly correlated with blood GSH levels, hence indicating blood GSH levels as a possible surrogate marker for GST activity in tumor tissues.

FIG. 1: correlation between GST activity in tumor tissue and GSH levels in matched whole blood specimens from lung cancer patients.

Figure 2:
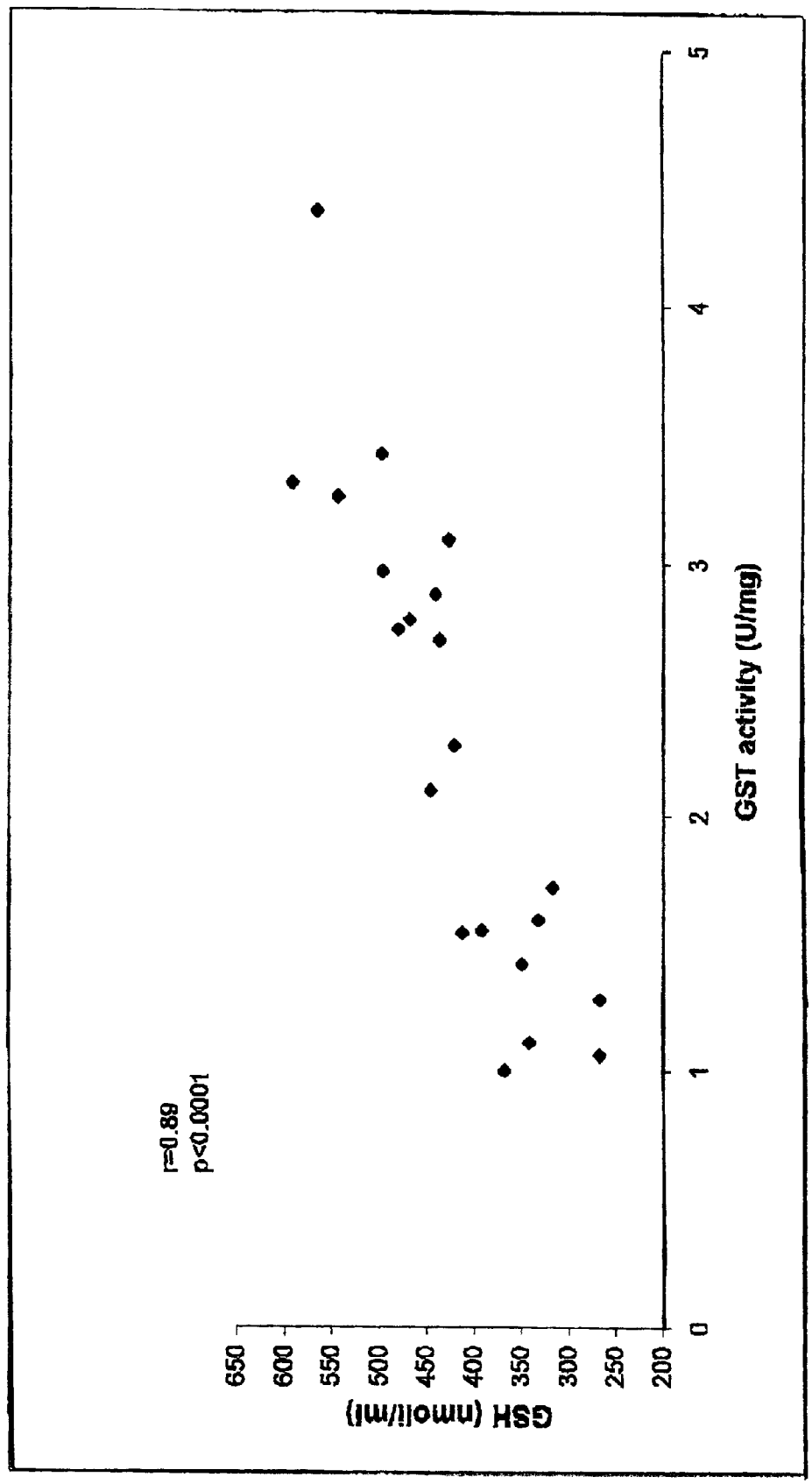

FIG. 2: correlation between GST activity in tumor tissue and GSH levels in matched whole blood specimens from head and neck cancer patients.

Therefore, it is a first object of the present invention a method for predicting the sensitivity towards chemotherapy of a patient in need thereof, which comprises obtaining a blood sample from the patient and detecting the presence of blood glutathione (GSH) as a surrogate marker for glutathione-S-transferase (GST) activity in tumor tissues.

According to the method of the invention, it is thus possible to identify whether a given tumor is associated with GSH/GST over expression, hence allowing the selection of the most suitable antitumor therapy.

It is therefore a further object of the invention a method for selecting the proper chemotherapeutic treatment for a patient in need thereof, which first comprises predicting his sensitivity towards chemotherapy by obtaining a blood sample from the patient, detecting the presence of blood glutathione (GSH) as a surrogate marker for glutathione-S-transferase (GST) activity in tumor tissues, determining whether the blood GSH levels fall within a range indicative of a potential for the patient to exhibit de novo or later progression to resistance to chemotherapeutic agents, and selecting a suitable and effective chemotherapeutic treatment.

In other words, once the blood levels of GSH being thus detected are so high to indicate, for the patient, the possibility of exhibiting resistance to conventional chemotherapeutic agents, for instance alkylating agents, anthracyclines or platinum complexes, a suitable and effective chemotherapeutic treatment, based on the above GSH levels, might comprise the administration of an antitumor agent which is effective in the treatment of those tumors over expressing GSH/GST.

In this respect, the compound N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4[(2-bromoacryloyl)amino]-1-methyl-1H-pyrrole-2-carboxamide (internal code PNU 166196), and pharmaceutically acceptable salts thereof, recently appeared to be effective in the treatment of a tumor known to be poorly responsive or resistant to conventional antitumor therapies and described in the literature as potentially over-expressing GSH/GST.

For a general reference to the above compound of formula

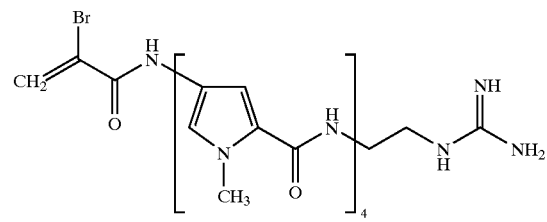

and to its effectiveness against tumors over expressing GSH/GST system, see the international patent application WO 98/04524 and PCT/EP01/04470 (the latter yet unpublished, filed on Apr. 19, 2001 and claiming priority from UK patent application No. 0011059.3, filed on May 8, 2000), both in the name of the Applicant itself and herewith incorporated by reference.

Preferably, a suitable therapy could thus comprise the administration to a patient in need thereof, of the proper amounts of the compound PNU 166196, for instance according to the administration schedule reported in the still unpublished patent application U.S. Ser. No. 09/676770, filed on Oct. 2, 2000 in the name of the Applicant itself and herewith incorporated by reference.

According to a preferred embodiment of the invention, the above method for predicting the sensitivity towards chemotherapy could be advantageously used in several tumor forms including, for instance, gastrointestinal tumors, uterine and ovarian cancers, head and neck cancer, lung carcinomas, sarcomas and liver tumors.

Even more preferably, the said tumor is selected from lung, head and neck cancer.

In addition, the above method may also be applied to select the proper antitumor therapy as a second line therapy, for instance once a previous chemotherapy treatment, for example a first-line chemotherapy treatment with conventional antitumor agents, e.g. alkylating agents, platinum derivatives or anthracyclines, failed to give the expected results because of the occurrence, among other effects, of the aforementioned resistance effects.

Several methods are known in the art for the assay of GSH and related kits are commercially available.

According to the present invention, therefore, any commercially available kit for detecting GSH levels in blood samples may be conveniently employed.

In this respect, it is a further object of the invention the use of a kit for determining blood GSH levels as a surrogate marker for GST activity in tumor tissues.

With the aim of illustrating the present invention, without posing any limitation to it, the following experimental part is now given.

EXPERIMENTAL PART

The following experimental part was used to demonstrate the strong correlation existing between the GSH levels in blood versus the GST activity in tumor tissues, so as to render GSH detection in blood as a surrogate marker for GST levels in tumor tissues.

As formerly indicated, FIGS. 1 and 2 clearly show the above correlations between GSH levels in blood of lung cancer patients and head and neck cancer patients, with the GST activities in tumor tissues of the said patients.

Tissue and blood samples from 29 patients with lung cancer (NSCLC) and 23 patients with head and neck cancer (SCC) were enrolled, as per the following table I.

TABLE I

| Principal characteristics | Patient series | |
|---|---|---|
| | Head and neck cancer | Lung cancer |
| No. | 23 | 29 |
| Age | 56 (29–72) | 67 (28–80) |
| Sex | 16 m - 7 f | 24 m - 5 f |
| Tumor type | SCC | 26 (NSCLC) |
| | | 2 (lung adenocarcinoma) |
| | | 1 (spino cell.) |

Sampling Modalities

Tissue from primary or relapsed tumor. A sample ($\leq 200$ mg) of tumor tissue adjacent to the sample submitted for histological examination was collected from each patient. Tissue samples were put immediately in crushed ice. Samples were frozen in liquid nitrogen within 30 minutes (max 1 hour) from the excision.

Blood (before treatment of the primary tumor or at time of failure). Blood (15 ml) was collected in a pre-chilled syringe and processed as follows.

3 ml were dispensed in $K_3$EDTA (or ACD-solution A) tubes and stored at $-20°$ C. (whole blood).

Analytical Methods

GSH quantity. GSH level in cytosol and whole blood samples was measured by a commercially available GSH assay kit (Cayman, Ann Arbor, Mich., USA). This kit utilizes an enzymatic recycling method based on the reaction between GSH and DTNB that produces a yellow coloured compound (TNB). The rate of TNB production is directly proportional to the concentration of GSH in the sample. Measurement of the absorbance of TNB at 405 nm provides an accurate estimation of GSH in the sample.

Before assaying, samples were deproteinated with 10% metaphosphoric acid (MPA) to avoid interferences due to sulfhydryl groups on the proteins in the assay. 50 $\mu$l of the deproteinated sample (whole or diluted 1:3 with kit Wash Buffer) were assayed in duplicate according to manufacturer's instructions. GSH concentration was measured by comparison with a standard curve obtained by plotting the absorbance at 25 min vs. GSH concentration (nmol/ml). Cytosol GSH levels were normalised for protein content (nmol/mg).

GST activity. 10 $\mu$l of cytosol was analysed by a commercially available assay kit (Novagen, Darmstadt, Germany) according to manufacture's instructions. This kit is designed to perform a colorimetric-enzymatic assay of glutathione S-transferase (GST): a sample is combined with 1-chloro-2,4-dinitrobenzene (CDNB) substrate in the supplied reaction buffer and the absorbance of the reaction is monitored at $\lambda = 340$ nm. The rate of change in $A_{340}$ is proportional to the amount of GST activity in the sample.

The absorbance at 340 nm was monitored every 30 sec. over a period of 5 min for cytosol samples.

GST activity of all samples was compared with a standard (cytosol of human placenta) and was measured as U*/mg prot for cytosol sample.

*U=(dA/min of 10 $\mu$l placenta)/mg prot of placenta

Assay Validation

The validation of the methods was planned taking into account: sensitivity, specificity, precision (intra-assay, inter-assay, inter-batch), calibration range, reagent stability, and analyte stability in different storage conditions.

GSH

Analytical sensitivity, evaluated as the mean +3 SD of 8 replicates of the zero standard, was 0.33 nmol/ml.

Functional sensitivity was evaluated by plotting the imprecision profile of the method.

The minimum concentration with a C.V. less then 10% was 0.4 nmol/ml.

Assay kit is based on a reaction between GST-reductase and DTNB that reacts with all groups —SH contained in the sample. A high specificity is expected since: all thiol protein groups are removed by deproteination; GST-reductase is a specific enzyme for GSH substrate; the reaction is monitored at $\lambda = 405$ that is specific for GSH. No further confirmation experiments were thus performed.

Precision was evaluated analysing, for 5 consecutive runs, a duplicate of whole blood.

We obtained an inter-assay C.V. below 12% while the intra-assay C.V. was below 5% of variability (tables 5 and 6).

The calibration curve ranges between 0.6–40 nmol/ml.

All reagents must be stored at $+4°$ C. until expiration date indicated by manufacturers.

After opening, reagents are stable for 2 weeks at $+4°$ C.

Samples and deproteinated samples are stable up to 6 months if stored at $-80°$ C. and $-20°$ C. respectively.

GST Activity

Analytical sensitivity was evaluated by 8 replicates of the zero standard and resulted 0.0055 U/ml.

Functional sensitivity was evaluated on 8 replicates of low activity sample. Since C.V. of replicates was less than 10% (9.2%) the corresponding mean activity level (0.008 U of activity) was considered as functional sensitivity.

Activity assay kit is based on a enzymatic reaction between glutathione-s transferase and CDNB, that is a specific substrate of the enzyme. Accordingly the specificity of the method used is largely demonstrated in literature (Habig W. H., 1974; Smith D. B., 1988). We therefore did not perform further confirmatory experiments.

Accuracy was evaluated with dilution test of a cytosol sample. Recovery was between 112% and 133%.

Precision was evaluated on 2 cytosol samples with two different activity levels. Four replicates of the samples were assayed on 5 different runs. Inter and intra-assay C.V. were respectively under 9% of variability in high activity level sample and under 14% of variability in low activity level sample.

The calibration curve ranges between 0.01–0.4 dA/min

All reagents must be stored at −20° C. until expiration date indicated by manufacturers, samples are stable up to 6 months if stored at −80° C.

GSH Results

GSH levels were measured in whole blood from 29 patients with lung cancer and 22 with head and neck cancer. Mean level in blood is 516 nmol/ml (S.D.=117) in lung cancer and 428 nmol/ml (S.D.=97) in head and neck cancer.

TABLE II

GSH levels

| Summary Statistics | | Whole blood (nmol/ml) |
|---|---|---|
| Overall | mean | 477 |
| | median | 458 |
| | 10°–90°% | 350–620 |
| | n | 52 |
| | paired Wilcoxon test | <0.0001 (0.0001) |
| Lung cancer | mean | 516 |
| | median | 494 |
| | 10°–90°% | 383–681 |
| | n | 29 |
| | paired Wilcoxon test | 0.0004 (0.0001) |
| Head and neck cancer | mean | 428 |
| | median | 426 |
| | 10°–90°% | 317–566 |
| | n | 23 |
| | paired Wilcoxon test | 0.03 (0.0532) |

GST Activity

Total GST activity was measured in cytosol but not in plasma sample, because of low levels of the GST enzymes in this matrix. In fact we have tested 21 plasma samples of 29 available lung cancer patients and 15 of 23 head and neck cancer patients: GST activity was close to sensibility threshold of the method being not detectable in 11/21 lung and 3/15 head and neck samples.

GST activity was measured in 29 tissue samples of lung cancer and in 22 of head and neck cancer. Mean activity is 1.72 U/Mg (S.D.=0.89) in lung cancer tissue. In head and neck, mean activity is 2.61 U/mg (S.D.=1.74).

TABLE III

GST activity

| Summary Statistics | | Cancer tissue U/mg |
|---|---|---|
| Overall | mean | 2.1 |
| | median | 1.72 |
| | 10°–90°% | 1.06–3.31 |
| | n | 51 |
| | paired Wilcoxon test | <0.0001 (0.0001) |
| Lung cancer | mean | 1.72 |
| | median | 1.37 |
| | 10°–90°% | 0.87–2.97 |
| | n | 29 |
| | paired Wilcoxon test | 0.0002 (0.0001) |
| Head and neck cancer | mean | 2.61 |
| | median | 2.49 |
| | 10°–90°% | 1.11–3.42 |
| | n | 22 |
| | paired Wilcoxon test | 0.02 (0.0789) |

Conclusions

The evaluated methods are reliable and robust for routine use in tissue extracts (GST activity) and in whole blood (GSH level).

A highly significant positive correlation was found between whole blood GSH and tissue GST activity.

In particular, the GST activity in cancer tissue vs. GSH level in whole blood resulted to be correlated in lung cancer (r=0.53, p=0.003, FIG. 1) and in head and neck cancer (r=0.89, p<0.0001; FIG. 2).

TABLE IV

GST activity in cancer tissue vs. whole blood GSH levels

| Tumor | Spearman Correlation | p value |
|---|---|---|
| Lung | 0.53 | 0.004 |
| Head and neck | 0.89 | <0.0001 |

The above results clearly provide evidence that the GSH levels in blood samples of a cancer patient can be used as a surrogate marker for GST activities in tumor tissues, thus allowing to predict whether the patient responsiveness to chemotherapy is associated with GSH/GST system over expression.

What is claimed is:

1. A method for predicting a sensitivity towards chemotherapy, of a patient in need thereof, which comprises obtaining a blood sample from the patient; measuring levels of blood glutathione (GSH) as a surrogate marker for glutathione-S-transferase (GST) activity in tumor tissues; determining whether blood GSH levels fall within a range indicative of a potential for the patient to exhibit de novo or later progression to resistance to chemotherapeutic agents; and predicting the sensitivity towards chemotherapy of the patient.

2. The method of claim 1 which further comprises predicting whether a tumor suffered by the patient is associated with GST over expression.

3. The method of claim 2 wherein the tumor is selected from the group consisting of gastrointestinal tumors, uterine and ovarian cancers head and neck cancer, lung carcinomas, sarcomas and liver tumors.

4. The method of claim 3 wherein the tumor is selected from the group consisting of head, neck and lung cancer.

5. A method for selecting a chemotherapeutic treatment for a patient in need thereof, which comprises obtaining a blood sample from the patient, measuring levels of blood glutathione (GHS) as a surrogate marker for glutathione-S-transferase (GST) activity in tumor tissues, determining whether blood GSH levels fall within a range indicative of a potential for the patient to exhibit de novo or later progression to resistance to chemotherapeutic agents, and selecting a suitable and effective chemotherapeutic treatment based on the GSH levels.

6. The method of claim 5 for selecting the proper chemotherapeutic treatment for a patient suffering a tumor selected from the group consisting of gastrointestinal tumors, uterine and ovarian cancers head and neck cancer, lung carcinomas, sarcomas and liver tumors.

7. The method of claim 6 wherein the tumor is selected from the group consisting of head, neck and lung cancer.

8. The method of claim 5 which, based on the blood GSH levels, allows one to select the proper chemotherapeutic treatment, further comprises administering to the patient in need thereof the compound N-(5{[(5-{[(5-{[(2-{[amino(imino)methyl]amino}ethyl)amino]carbonyl}-1-methyl-1H-pyrrol-3-yl)amino}carbonyl}-1-methyl-1H-pyrrol-3yl)amino]carbonyl}-1-methyl-1H-pyrrol-3-yl)-4-[(2-bromoacryloyl)amino]-1-methyl-1H-pyrrole-2-2carboxamide or a pharmaceutically acceptable salt thereof or, alternatively, of a conventional antitumor agent.

9. The method of claim 8 wherein the conventional antitumor agent is selected from the group consisting of alkylating agents, anthracyclines and platinum derivatives.

10. A method for treating a patient suffering from a tumor over expressing GSH/GST system, which comprises obtaining a blood sample from the patient, measuring levels of blood glutathione (GHS) as a surrogate marker for glutathione-S-transferase (GST) activity in tumor tissues, determining whether the blood GSH levels fall within a range indicative of a potential for the patient to exhibit de novo or later progression to resistance to chemotherapeutic agents, and treating the patient by administering to the patient an effective amount of N-(5{[(5-{[(5-{[(2-{[amino(imino)methyl]amino}ethyl)amino]carbonyl}-1-methyl-1H-pyrrol-3-yl)amino}carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-2carboxamide or a pharmaceutically acceptable salt thereof.

11. The method of claim 10 wherein the tumor is selected from the group consisting of gastrointestinal tumors, uterine and ovarian cancers head and neck cancer, lung carcinomas, sarcomas and liver tumors.

12. The method of claim 11 wherein the tumor is selected from the group consisting of head, neck and lung cancer.

* * * * *